United States Patent [19]

Chen et al.

[11] Patent Number: 5,600,042
[45] Date of Patent: Feb. 4, 1997

[54] PROCESS FOR THE PRODUCTION OF VINYL CHLORIDE

[76] Inventors: Wu-Chi Chen; Harvey R. Chen, both of 859 Brittmoore Rd., Houston, Tex. 77079-3601

[21] Appl. No.: 429,786

[22] Filed: Apr. 27, 1995

[51] Int. Cl.$^6$ .............................. C07C 21/00; C07C 17/04
[52] U.S. Cl. .............................................. 570/230; 570/216
[58] Field of Search ...................................... 570/230, 216

[56] References Cited

U.S. PATENT DOCUMENTS

| | | | |
|---|---|---|---|
| 2,525,589 | 10/1950 | Cass | 570/230 |
| 3,480,534 | 11/1969 | Harmer et al. | 570/230 |

FOREIGN PATENT DOCUMENTS

| | | | |
|---|---|---|---|
| 701508 | 1/1965 | Canada | 570/230 |
| 1050540 | 12/1966 | United Kingdom | 570/230 |

*Primary Examiner*—Alan Siegel

[57] ABSTRACT

The purpose of this invention is to describe a new process for the manufacture of choroethene ($C_2H_3Cl$). This new process involves the use or ethylene ($C_2H_4$) as a feedstock. Highly chlorinated ethenes or methanes are used as chlorinating agents. The corresponding less chlorinated ethenes or methanes are recovered as co-products or recycled to the process to produce additional chloroethene. The distribution of the products may be adjusted so that chloroethene is the major product.

20 Claims, 3 Drawing Sheets

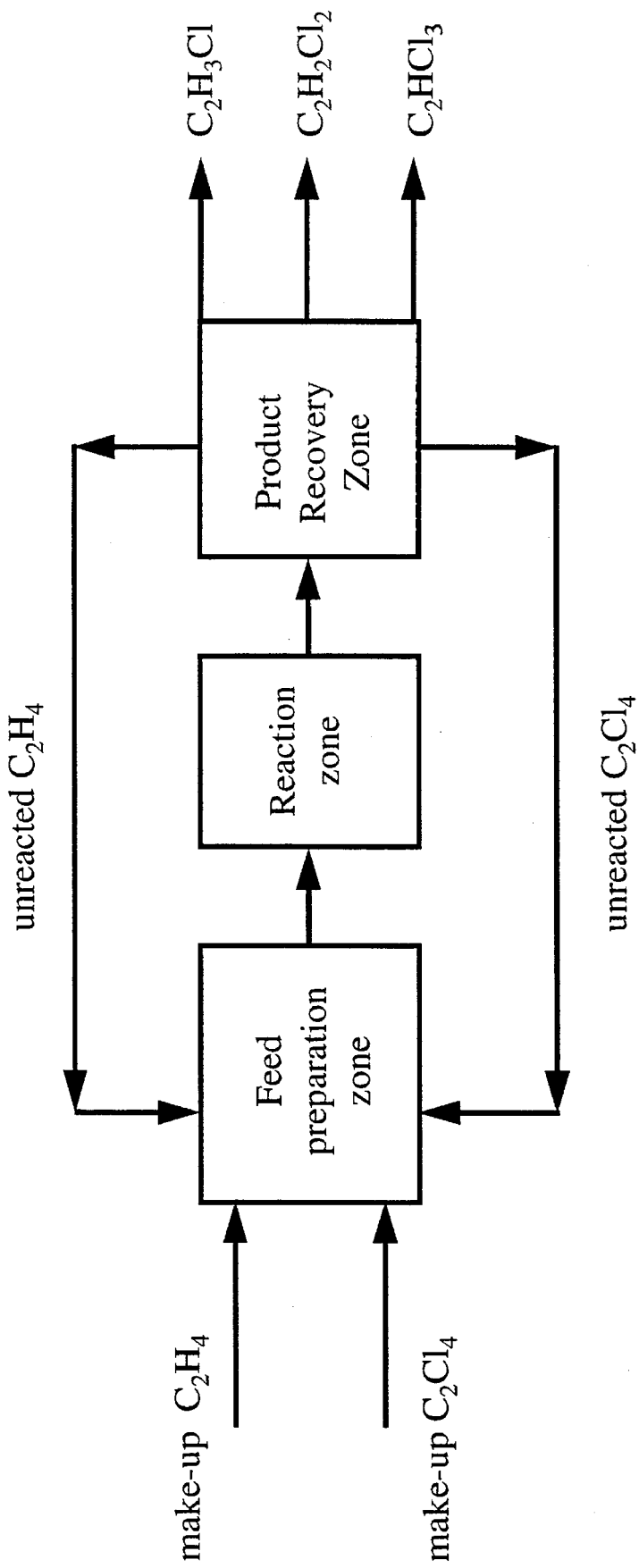
Figure 1. Block diagram for the new process, using $C_2Cl_4$ as feed.

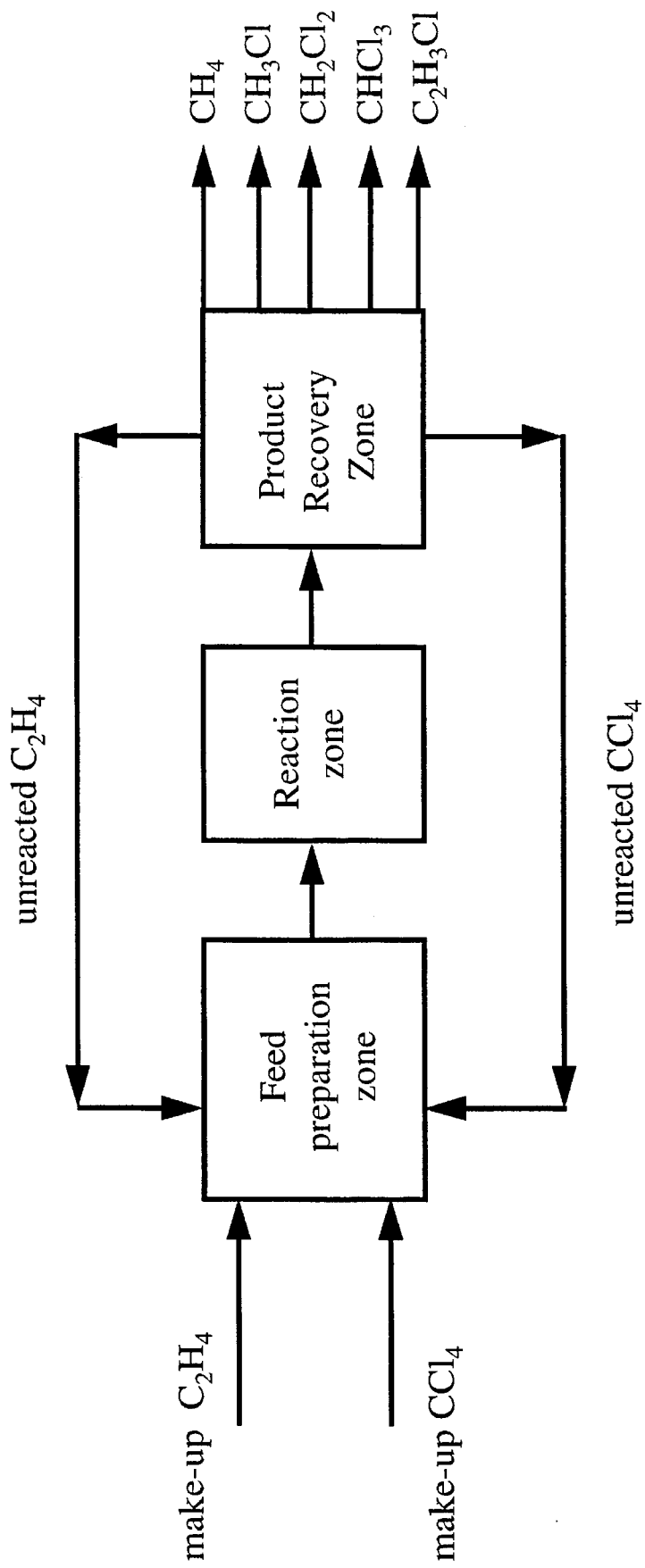
Figure 2. Block diagram for the new process, using $CCl_4$ as feed.

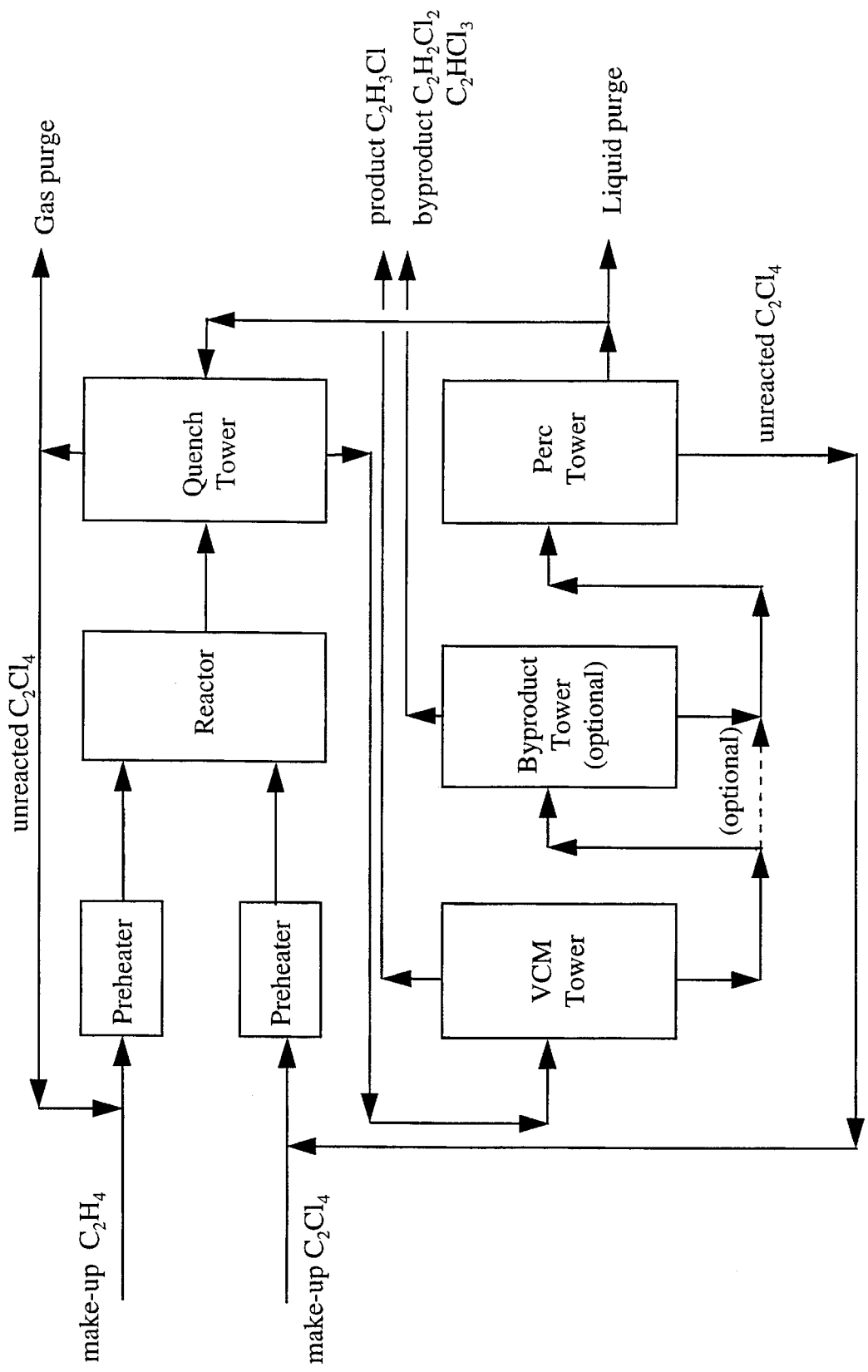
Figure 3: Schematic diagram of the new process.

PROCESS FOR THE PRODUCTION OF VINYL CHLORIDE

FIELD OF THE INVENTION

This invention describes a new process for the manufacture of $C_2H_3Cl$ from ethylene. $C_2Cl_4$ or $CCl_4$ is used as a principal chlorinating agent. Less chlorinated ethenes or methanes are recovered as co-products or recycled as chlorinating agents. The process can be adjusted so that the manufacture of a major product, chloroethene, is maximized.

BACKGROUND OF INVENTION

Chloroethene, commonly known as vinyl chloride monomer (VCM), is one of the world's major commodity chemicals. It is used in the manufacture of polyvinyl chloride (PVC), one of the oldest and most important polymers.

The first commercial process for large-scale production of chloroethene was developed in the 1930's. It involved the reaction of acetylene with hydrogen chloride.

$$C_2H_2 + HCl \rightarrow C_2H_3Cl \tag{1}$$

U.S. Pat. No. 2,779,804 disclosed such a process. The acetylene feedstock for this method was manufactured by the reaction between calcium carbide and water. The disadvantages of this process were the high cost and scarcity of acetylene.

In the 1950's, a second commercial process was developed using ethylene as well as acetylene. Ethylene is first chlorinated by mixing it with pure chlorine gas, yielding ethylene dichloride, $C_2H_4Cl_2$ (EDC).

$$C_2H_4 + Cl_2 \rightarrow C_2H_4Cl_2 \tag{2}$$

The ethylene dichloride is then subjected to high temperatures in order to crack it, producing $C_2H_3Cl$ as a product and HCl as a byproduct.

$$C_2H_4Cl_2 \rightarrow C_2H_3Cl + HCl \tag{3}$$

To recover its chlorine the HCl is used to hydrochlorinate acetylene, as shown in equation (1). U.S. Pat. No. 3,506,727 disclosed this process. The need for high-cost acetylene remains as a disadvantage of this second commercial process.

The commercial process that is currently employed by major VCM producers is a balanced process. It occurs in three basic steps: direct chlorination, pyrolysis, and oxychlorination. Ethylene is chlorinated with pure chlorine gas to produce EDC, as shown in equation (2) above. EDC is then cracked to produced vinyl chloride monomer and HCl, as shown in equation (3) above. HCl produced in EDC cracking is combined with ethylene and oxygen in an oxychlorination step that produces additional EDC and the byproduct water.

$$2\,HCl + C_2H_4 + \tfrac{1}{2}O_2 \rightarrow C_2H_4Cl_2 + H_2O \tag{4}$$

The EDC produced in oxychlorination is recycled for pyrolysis to manufacture additional vinyl chloride, while the water, after wastewater treatment, is discharged into the environment. U.S. Pat. Nos. 3,504,043; 5,175,382; 5,099,085; 4,587,230; and 3,799,998 disclosed such a process.

The primary disadvantage present in this commercial process is the cost and energy efficiency of feedstock. Ethylene, which is employed in the oxychlorination step to recover the chlorine value from HCl, is a relatively expensive feedstock. The gases released from the oxychlorination vent also contain more than 100 ppm of vinyl chloride monomer (VCM), which has been shown to be an atmospheric health hazard. In addition, coking of the furnace tubes in the plant increases significantly with the more severe cracking conditions. Plants using this process must dispose of significant amounts of chlorinated hydrocarbon waste.

Several processes have been developed to use cheaper feedstocks for vinyl chloride production. U.S. Pat. Nos. 5,097,083 and 4,300,005 proposed the use of methane or ethane as feedstocks. Methods designed to reduce coking and promote cracking in the furnace have been disclosed in U.S. Pat. Nos. 5,210,345; 4,380,682; 4,590,317; 4,590,318; 4,584,420; and 4,225,520.

Various other processes for the production of vinyl chloride have been disclosed. U.S. Pat. No. 2,681,372 disclosed vinyl chloride production from $C_2H_4$. U.S. Pat. No. 4,256,719 disclosed a process for the production of vinyl chloride without the consumption of elemental chlorine produced by electrolysis.

In commerce, 1,2-dichloroethenes are used as feedstocks for the production of tri-and tetra-chloroethenes. They are obtained as unwanted byproducts from other chlorination processes and, therefore, are not deliberately produced in large quantities. 1-dichloroethene is used to produce 1,1, 1-trichloroethane and poly (vinylidene chloride). It is manufactured by cracking 1,1,2-trichloroethane, a waste byproduct from the existing VCM process. Trichloroethene is used as a solvent for extraction or vapor degreasing. It is produced by chlorinolysis and oxychlorination processes.

Chloromethanes are important chemicals. They are used not only as industrial solvents but also as chemical intermediates. Chlorinated methanes are produced by thermal chlorination of methane. Byproduct HCl is recovered and sold as concentrated hydrochloric acid, if its market is available. HCl can also be disposed of, for example, by reacting with methanol to produce additional $CH_3Cl$.

It is therefore an objective of the present invention to provide a new method for the production of chloroethene that minimizes or eliminates the disadvantages of the existing methods. Other objectives and advantages of the invention will become apparent film the following description and the accompanying drawings:

SUMMARY OF THE INVENTION

For the new process of manufacturing chloroethene, two types of chlorinating agents are used. These are highly chlorinated ethenes and methanes. Using chlorinated ethenes, three major reactions are carried out. The first step involves a reaction between $C_2H_4$ and $C_2Cl_4$ to produce chloroethene and $C_2HCl_3$.

$$C_2H_4 + C_2Cl_4 \rightarrow C_2H_3Cl + C_2HCl_3 \tag{5}$$

The second reaction occurs as trichloroethene reacts with ethylene in a fashion similar to the first reaction. This step yields another product, $C_2H_2Cl_2$, and additional $C_2H_3Cl$.

$$C_2H_4 + C_2HCl_3 \rightarrow C_2H_3Cl + C_2H_2Cl_2 \tag{6}$$

The final step of this process involves the reaction between the dichloroethenes and ethylene in a manner similar to the previous two steps, yielding $C_2H_3Cl$ as a product.

$$C_2H_4 + C_2H_2Cl_2 \rightarrow 2\,C_2H_3Cl \tag{7}$$

The process may be adjusted so that the appropriate combination of products can be manufactured. By recycling $C_2H_2Cl_2$ and $C_2HCl_3$ for reaction with $C_2H_4$, a single product, i.e. $C_2H_3Cl$, can be produced. The overall reaction is $$3C_2H_4 + C_2Cl_4 \rightarrow 4C_2H_3Cl \quad (8)$$

Byproducts $C_2H_2Cl_2$ and/or $C_2HCl_3$ can also be recovered and used, via chlorinolysis or oxychlorination, to produce $C_2Cl_4$ for the new process.

Using chlorinated methanes, four major reactions are carried out. The first step involves a reaction between $C_2H_4$ and $CCl_4$ to produce chloroethene and $CHCl_3$.

$$C_2H_4 + CCl_4 \rightarrow C_2H_3Cl + CHCl_3 \quad (9)$$

The second reaction occurs as trichloromethane reacts with ethylene in a fashion similar to the first reaction. This step yields additional $C_2H_3Cl$ and another product, $CH_2Cl_2$.

$$C_2H_4 + CHCl_3 \rightarrow C_2H_3Cl + CH_2Cl_2 \quad (10)$$

The third step of this process involves the reaction between dichloromethane and ethylene in a manner similar to the previous two steps, yielding $C_2H_3Cl$ and $CH_3Cl$ as products.

$$C_2H_4 + CH_2Cl_2 \rightarrow C_2H_3Cl + CH_3Cl \quad (11)$$

The final step of this process involves the reaction between monochloromethane and ethylene in a manner similar to the previous three steps, yielding $C_2H_3Cl$ and $CH_4$ as products.

$$C_2H_4 + CH_3Cl \rightarrow C_2H_3Cl + CH_4 \quad (12)$$

The process may be adjusted so that appropriate combination of products can be manufactured. By recycling $CH_3Cl$, $CH_2Cl_2$, and $CHCl_3$ for reaction with $C_2H_4$, a single product, i.e. $C_2H_3Cl$, can be maximized. The overall reaction is $$4C_2H_4 + CCl_4 \rightarrow 4C_2H_3Cl + CH_4 \quad (13)$$

Byproducts $CH_3Cl$, $CH_2Cl_2$ and/or $C_2HCl_3$ can also be recovered and used, via chlorination or oxychlorination, to produce $CCl_4$ for the new process.

Several advantages exist that make this new process/ favorable as compared to the method using direct chlorination and oxychlorination of ethylene, and cracking of the resulting EDC. First of all, a portion of the ethylene feedstock requirement can be met with $C_2Cl_4$, which can be obtained from cheaper raw materials, such as ethane or other hydrocarbons. The oxychlorination process can be eliminated if tetrachloroethene or carbon tetrachloride used in the new process is obtained via carbon disulfide or via chlorinolysis. Also, transportation of chlorine gas to distant vinyl chloride producers can be made in the form of $C_2Cl_4$ or $CCl_4$, which are easier and safer to handle and ship. Another advantage is that chlorinated hydrocarbon waste byproducts generated in enormous quantities in other chlorinated hydrocarbon industries can be used as sources of chlorine for the production of $C_2Cl_4$ or $CCl_4$ for this new process. Therefore, the new process provides an economically and ecologically important method for the disposal and utilization of waste byproducts from the chlorinated hydrocarbon industries.

DESCRIPTION OF THE INVENTION

The new process is illustrated in greater detail in the attached three drawings. Referring to the accompanying drawings, FIG. 1 is a block diagram for manufacturing $C_2HCl_3$, $C_2H_2Cl_2$, and $C_2H_3Cl$, using $C_2H_4$ and $C_2Cl_4$ as feeds. It includes feed preparation, reaction, and product recovery zones. The drawing shows reactants being combined prior to entering the reactor, with product recovery and the recycle of unconsumed reactants.

In the feed preparation zone, make-up $C_2Cl_4$ and $C_2H_4$ are combined with recycled ethylene and tetrachloroethene. If the $C_2HCl_3$ and $C_2H_2Cl_2$ products are not needed, they are recycled with unreacted $C_2Cl_4$. The resulting $C_2Cl_4$-$C_2H_4$ stream is fed into the reaction zone.

The temperature within the reactor can be controlled, for example, by excess $C_2H_4$, heat exchangers, or reactor feed temperatures. Effluent from the reactor is a mixture of chloroethene, trichloroethene, dichloroethenes, and unreacted ethylene and $C_2Cl_4$. It is then sent to the product recovery zone.

In the product recovery zone, the reactor effluent mixture is cooled to separate the products and the unreacted reagents. The gaseous ethylene which is not consumed in the reaction is recycled to the reaction feed preparation zone. $C_2H_3Cl$ is recovered as a product. $C_2HCl_3$ and $C_2H_2Cl_2$ are recovered as products or recycled back, together with unreacted $C_2Cl_4$, to react with additional ethylene.

Referring to the accompanying drawings, FIG. 2 is a block diagram for manufacturing $C_2H_3Cl$ using $CCl_4$ as the principal chlorinating agent. It includes feed preparation, reaction, and product recovery zones. The drawing shows reactants being combined prior to the reactor, with product recovery and the recycle of unconsumed reactants.

In the feed preparation zone, make-up $C_2H_4$ and $CCl_4$ are combined with recycled ethylene and carbon tetrachloride. If products $CHCl_3$, $CH_2Cl_2$, and $CHCl_3$ are not needed, they are recycled with unreacted $CCl_4$. The resulting $C_2H_4$-$CCl_4$ stream is fed into the reaction zone.

The temperature within the reactor can be controlled by excess $C_2H_4$, heat exchangers, or reactor feed temperatures. Effluent from the reactor is a mixture of chloroethene, dichloromethane, trichloromethane, chloromethane, methane, and unreacted ethylene and $CCl_4$. It is then sent to the product recovery zone.

In the product recovery zone, the reactor effluent mixture is cooled to separate the products and the unreacted reagents. The gaseous ethylene which is not consumed in the reaction, after purge of byproduct methane, is recycled to the reaction feed preparation zone. $C_2H_3Cl$ is recovered as a product. $CH_3Cl$, $CH_2Cl_2$ and $CHCl3$ are recovered as products or recycled back, together with unreacted $CCl_4$, to react with additional ethylene. $CH_4$ is recovered as a byproduct.

Referring to the accompanying drawings, FIG. 3 is a schematic diagram of a representative process of this invention. More specifically, the drawing shows the feeds of ethylene and tetrachloroethene and the production of chloroethene. Two small streams, one gas and one liquid, are purged from the process to remove the undesirable byproducts and impurities introduced in the feeds. As described in the Summary of the Invention and in FIG. 2, carbon tetrachloride can also be used as feed to produce monochloroethene. However, it is not described in detail in FIG. 3. Many other variations of the process will also become apparent after following the description of this invention.

In FIG. 3, make-up ethylene and tetrachloroethene feeds, along with recycled ethylene and tetrachloroethene, are preheated and sent to the Reactor. Separate preheaters are used before the different feed streams are fed into the Reactor. This step controls the residence time and reduces tar formation. Make-up ethylene should contain only a minimum amount of other hydrocarbons in order to simplify product separation and recovery. The new process can be carried out at various pressures, for example, from 1 atm to 40 atm. However, higher operating pressures of about 5 to 20 atm are preferred because high pressure reduces equipment sizes and improves product recovery.

The ratio of ethylene to tetrachloroethene in feedstocks is an important factor product distribution. An excess amount of ethylene in feeds is preferred, as it reduces tar formation. An excess amount of tetrachloroethene would be used to enhance the production of di- and trichloroethenes. Steam and oxygen should be excluded from the feedstocks because they promote decomposition and polymerization.

In the Reactor, reactions (5), (6), (7), and (8) proceed to the right-hand direction between 100° C. and 650° C. However, at extremely high temperatures above 650° C., excess amounts of undesirable byproducts are formed due to cracking. At operating temperatures much less than 100° C., the reaction rates would be too slow to be practical. The preferred operating temperature is between 350° C. and 550° C., where only a small amount of cracking of chloroethene occurs. Reaction at higher temperatures would require a shorter residence time to minimize tar formation, whereas lower temperatures would require catalysts to promote reactions.

The overall reaction for producing chloroethene in reaction (8) is slightly exothermic. Both adiabatic and isothermal reactors can be used. Reaction temperature can be controlled using a heat exchanger between two reactors. The heat exchanger can be eliminated if the Reactor is a back-mixed reactor and cooler feeds are used. A single reactor can also be used if it is designed with internal or external heat removal, such as preheating the incoming feeds. The reaction temperature can also be controlled using an excess amount of ethylene or tetrachloroethene in the reactor feeds.

Effluent from the Reactor is cooled to recover valuable products. Sensible heat from the reactor effluent can be recovered for use in other areas of the process. In FIG. 3, effluent from the Reactor is cooled with recirculating liquid tetrachloroethene in the Quench Tower. Off-gas from the Quench Tower contains unreacted ethylene. It is recycled to the Preheater. Liquid from the Quench Tower is sent to the VCM Tower, where chloroethene is distilled and recovered in overhead as a crude product, which can be further purified to meet product specifications. The heavier stream from the VCM Tower is sent to the Byproduct Tower, where dichloroethenes and trichloroethene are distilled and recovered as byproducts. Dichloroethenes and trichloroethene can also be used to produce tetrachloroethene for the new process. The bottom stream from the Byproduct Tower is fed to the Perc Tower and distilled to recover $C_2Cl_4$ for recycle to the Reactor. The heavier stream from the Perc Tower, after the removal of a small purge stream, is recycled to the Quench Tower. If dichloroethenes and trichloroethene are not needed, the Byproduct Tower is bypassed, and the bottom stream from the VCM Tower is fed to the Perc Tower.

The use of $CCl_4$ as the chlorinating agent in the new process is not shown in FIG. 3. It would require more steps in product recovery. The reaction shown in equation (12) produces methane. Separation of unreacted $C_2H_4$ and byproduct methane can be achieved by cryogenic means. If $CH_3Cl$ is to be recovered as a byproduct, its separation from the main product VCM, which has a normal boiling point very close to that of $CH_3Cl$, can be achieved by distillation. Although product recovery is more complicated, the process is useful when chlorinated hydrocarbon wastes are available for the production of $CCl_4$ as a feedstock for the process.

We claim:

1. A process for the manufacture of $C_2H_3Cl$ consisting essentially of
   (a) the reaction of $C_2H_4$ with a chlorinating stream containing a highly chlorinated ethene, such as $C_2Cl_4$, $C_2HCl_3$, or $C_2HCl_2$, to produce $C_2H_3Cl$ and a corresponding less chlorinated ethene, such as $C_2HCl_3$ or $C_2H_2Cl_2$, and
   (b) the separation of the effluent from the reaction to recover $C_2H_3Cl$ as a product, recover unreacted $C_2H_4$ and said highly chlorinated ethene for recycling, and recover said less chlorinated ethene as another product.

2. A process according to claim 1 in which the reaction is operated at a temperature between about 100° C. and about 650° C. and at a pressure between about 1 atm absolute and about 40 atm absolute.

3. A process according to claim 1 in which the reaction is operated using a reactor feed of $C_2H_4$ to highly chlorinated ethene molar ratio between about 0.1 and about 15 to 1.

4. A process according to claim 1 in which said highly chlorinated ethene is $C_2Cl_4$ and said less chlorinated ethene is $C_2HCl_3$ or $C_2H_2Cl_2$.

5. A process according to claim 1 in which said highly chlorinated ethene is $C_2HCl_3$ and said less chlorinated ethene is $C_2H_2Cl_2$.

6. A process according to claim 1 in which said highly chlorinated ethene is $C_2H_2Cl_2$ and said less chlorinated ethene is $C_2H_3Cl$, which is recovered as the main product.

7. A process according to claim 1 in which said highly chlorinated ethene is a mixture of $C_2Cl_4$ and $C_2HCl_3$, and said less chlorinated ethene is a mixture of $C_2HCl_3$ and $C_2H_2Cl_2$.

8. A process according to claim 1 in which said less chlorinated ethene is recycled and reacted with $C_2H_4$ to produce additional $C_2H_3Cl$.

9. A process according to claim 1 in which said less chlorinated ethene is oxychlorinated with $HCl/Cl_2$ and oxygen to produce said highly chlorinated ethene for the process.

10. A process according to claim 1 in which said chlorinating stream contains $CCl_4$.

11. A process for the manufacture of $C_2H_3Cl$ consisting essentially of
    (a) the reaction of $C_2H_4$ with a chlorinating stream containing a highly chlorinated methane, such as $CCl_4$, $CHCl_3$, $CH_2Cl_2$, or $CH_3Cl$ to produce $C_2H_3Cl$ and a corresponding less chlorinated methane, such as $CHCl_3$, $CH_2Cl_2$, or $CH_3Cl$, and
    (b) the separation of the effluent from the reaction to recover $C_2H_3Cl$ as a product, recover unreacted $C_2H_4$ and said highly chlorinated methane for recycling, and recover said less chlorinated methane as another product.

12. A process according to claim 11 in which the reaction is operated at a temperature between about 100° C. and about 650° C. and at a pressure between about 1 atm absolute and about 40 atm absolute.

13. A process according to claim 11 in which the reaction is operated using a reactor feed of $C_2H_4$ to highly chlorinated methane molar ratio between about 0.1 and about 15 to 1.

14. A process according to claim 11 in which said highly chlorinated methane $CCl_4$ and said less chlorinated methane is $C_2HCl_3$, $CH_2Cl_2$, $CH_3Cl$ or $CH_4$.

15. A process according to claim 11 in which said highly chlorinated methane $CHCl_3$ and said less chlorinated methane is $CH_2Cl_2$, $CH_3Cl$ or $CH_4$.

16. A process according to claim 11 in which said highly chlorinated methane is $CH_2Cl_2$ and said less chlorinated methane is $CH_3Cl$ or $CH_4$.

17. A process according to claim 11 in which said highly chlorinated methane is $CH_3Cl$ and said less chlorinated methane is $CH_4$.

18. A process according to claim 11 in which said less chlorinated methane is recycled and reacted with $C_2H_4$ to produce additional $C_2H_3Cl$.

19. A process according to claim 11 in which said less chlorinated methane oxychlorinated with $HCl/Cl_2$ and oxygen to produce said highly chlorinated methane for the process.

20. A process according to claim 11 in which said chlorinating stream contains $C_2Cl_4$.

* * * * *